United States Patent [19]

Greengrass et al.

[11] Patent Number: 4,684,642
[45] Date of Patent: * Aug. 4, 1987

[54] 7-HYDROXYAMINOCEPHALOSPORIN ANTIBIOTICS

[75] Inventors: Colin W. Greengrass; David W. T. Hoople, both of Sandwich; Thomas T. Howarth, Margate, all of England

[73] Assignee: Pfizer Inc., New York, N.Y.

[*] Notice: The portion of the term of this patent subsequent to Aug. 4, 2004 has been disclaimed.

[21] Appl. No.: 836,771

[22] Filed: Mar. 5, 1986

Related U.S. Application Data

[63] Continuation-in-part of Ser. No. 749,915, Jun. 27, 1985.

[30] Foreign Application Priority Data

Dec. 18, 1985 [GB] United Kingdom ............... 8531202

[51] Int. Cl.$^4$ ................ C07D 501/57; A61K 31/545

[52] U.S. Cl. .................................. 514/201; 514/202; 514/203; 514/206; 514/207; 540/221; 540/222; 540/224; 540/227; 540/228

[58] Field of Search ................ 544/21; 514/201, 202, 514/203, 206, 207; 540/222, 221, 224, 227, 228

[56] References Cited

U.S. PATENT DOCUMENTS 4,297,488 10/1981 Christensen et al. ............... 544/21
4,609,652 9/1986 Milner ............................... 514/201

Primary Examiner—Nicholas S. Rizzo
Attorney, Agent, or Firm—Charles J. Knuth; Albert E. Frost; Robert K. Blackwood

[57] ABSTRACT

7α-Hydroxyamino-7β-[2-substituted-2-(acylamino)acetamido]cephalosporin antibiotics, pharmaceutically-acceptable salts and in vivo hydrolyzable esters thereof, a method of treating susceptible infections therewith, and intermediates therefor.

29 Claims, No Drawings

7-HYDROXYAMINOCEPHALOSPORIN ANTIBIOTICS

CROSS REFERENCE TO RELATED APPLICATION

This application is a continuation in part of co-pending application Ser. No. 749,915, filed June 27, 1985.

BACKGROUND OF THE INVENTION

This invention relates to cephalosporin antibiotics, and in particular to cephalosporins having a 7α-hydroxyamino substituent.

U.S. Pat. No. 4,297,488, primarily directed to "7α-Methoxy Cephalosporins", broadly discloses a literal infinity of cephalosporin antibiotics of the formula

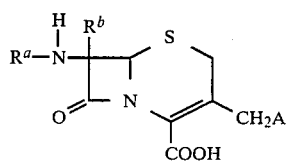

wherein $R^a$ represents any acyl group, A represents any organic radical or group, and $R^b$ represents any radical or group replacing hydrogen, and derivatives thereof such as esters, amides and salts. In extensive lists of possible groups which might correspond to $R^a$, $R^b$ and A in the above formula (still defining virtually infinite compounds) there is noted considerable overlap of possible groups A with present groups $R^2$ dfined below. While for $R^a$ none of the present alpha-(acylamino)acyl groups,

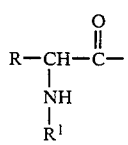

defined below, appear to be so listed, for $R^b$ one finds "hydroxyamino" listed among a list of some 100 different functional groups (which corresponds, through a wide variety of optional substituents, to an untold number of specific groups). No such compounds having $R^b$ as hydroxyamino are specifically disclosed or exemplified in this patent.

SUMMARY OF THE INVENTION

We have found a group of 7α-hydroxyamino cephalosporins which have unexpectedly good antibacterial properties, particularly against gram negative organisms, and including activity against beta-lactamase producing strains of bacteria.

Thus the present invention provides cephalosporin antibiotics of the formula

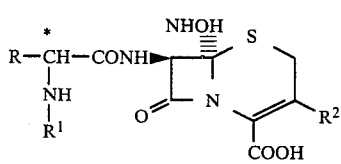

and their salts and esters, where R is phenyl, substituted phenyl, cyclohexenyl, cyclohexadienyl, $CH_3-CH(OH)-$, $CH_3-CH(OSO_3H)-$, $CH_3-CH(OCH_3)-$ or an optionally substituted aromatic 5- or 6-membered heterocyclic group containing 1, 2 or 3 heteroatoms each independently selected from O, S and N;

$R^2$ is $-CH_2OCOCH_3$, $-CH_2OCONH_2$, $-Cl$, $-F$, $-OCH_3$, $-CH_2N_3$, or a group of the formula:

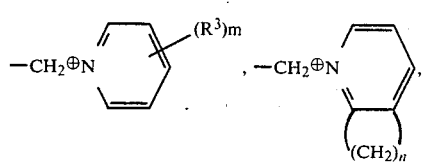

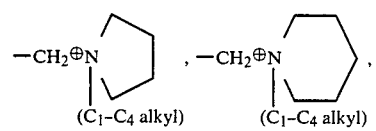

$-CH_2{}^{\oplus}N(C_1-C_4\ alkyl)_3$, or $-CH_2S.Het$, where each $R^3$ is independently H or $C_1-C_4$ alkl, m is 1 or 2, n is 3 or 4 and Het is an optionally substituted 5- or 6-membered heterocyclic group containing up to 4 heteroatoms selected from O, S and N, the heterocyclic group being optionally fused to an optionally substituted benzene ring or to a further 5- or 6-membered heterocyclic group containing up to 4 heteroatoms selected from O, S and N;

and $R^1$ is a group of the formula $-CONR^6R^7$ or $-COR^8$, where either (a) $R^6$ and $R^7$ are each independently H or $C_1-C_4$ alkyl, (b) $R^6$ is H or $C_1-C_4$ alkyl and $R^7$ is an optionally substituted 5 or 6 membered aromatic heterocyclic group containing 1 or 2 nitrogen atoms, or (c) $R^6$ and $R^7$ together with the nitrogen atom to which they are attached form an optionally substituted 5- or 6-membered heterocyclic group containing 1 or 2N atoms, and $R^8$ is optionally substituted phenyl, or a substituted or unsubstituted optionally benzo-fused 5- or 6-membered heterocyclic group, or the group $-CH_2NH-C(=NH)(4-pyridyl)$.

As particularly valuable compounds, we have now identified from among the above compounds of the formula (I), and their salts and esters, those compounds where R is an unsubstituted thiazolyl, thiadiazolyl, furyl or pyridyl group;

$R^2$ is $-CH_2OCOCH_3$, $-CH_2OCONH_2$ or a group of the formula:

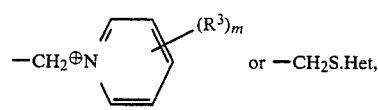

where m is 1 or 2 and each $R^3$ is independently H or $C_1-C_4$ alkyl; and Het is an optionally substituted 5- or 6-membered heterocyclic group containing up to 4 heteroatoms selected from O, S and N, the heterocyclic group being optionally fused to an optionally substituted benzene ring or to a further 5- or 6-membered heterocyclic group containing up to 4 heteroatoms selected from O, S and N;

and $R^1$ is a group of the formula:

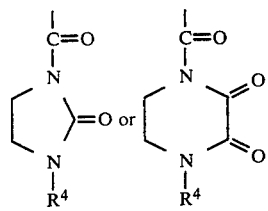

where $R^4$ is $C_1$-$C_4$ alkyl or —$SO_2$($C_1$-$C_4$ alkyl).

When $R^2$ is —$CH_2SHet$, "Het" is preferably an optionally substituted triazolyl, tetrazolyl, thiazolyl, isothiazolyl, oxazolyl, oxadiazolyl, triazinyl, thiadiazolyl, benzoxazolyl, benzothiazolyl, or tetrazolopyridazinyl group. Preferred substituents are $C_1$-$C_4$ alkyl, $C_1$-$C_4$ alkoxy, halo, oxo or a group of the formula —$(CH_2)_pR^5$ where p is 0, 1, 2 or 3 and $R^5$ is —COOH, —$OSO_2OH$, —$SO_2OH$, —$PO_3H_2$ or —OH, with the proviso that p is not zero when Het is tetrazolyl. With hydroxy and oxo substituents tautomerism may of course occur. "Halo" means F, Cl, Br or I.

The more preferred "Het" groups are attached to the adjacent S atom by a carbon atom of the heterocyclic ring and are (i) thiadiazolyl optionally substituted by $C_1$-$C_4$ alkyl or 2-hydroxyethyl (ii) tetrazolyl optionally substituted by $C_1$-$C_4$ alkyl, carboxymethyl, sulphomethyl, 2-hydroxyethyl, hydroxysulphonyloxymethyl or 2-(hydroxysulphonyloxy)ethyl (iii) thiazolyl optionally substituted by 1 or 2 substituents each selected from $C_1$-$C_4$ alkyl and carboxymethyl (iv) isothiazolyl optionally substituted by 1 or 2 substituents each selected from hydroxy and carboxy (v) benzothiazolyl or benzoxazolyl optionally substituted by hydroxy, $C_1$-$C_4$ alkoxy or halo (vi) tetrazolopyridazinyl optionally substituted by carboxy (vii) triazinyl optionally substituted by $C_1$-$C_4$ alkyl and/or by 1 or 2 oxo or hydroxy groups and (vii) triazolyl optionally substituted by carboxymethyl.

The preferred individual groups represented by "Het" are as follows:

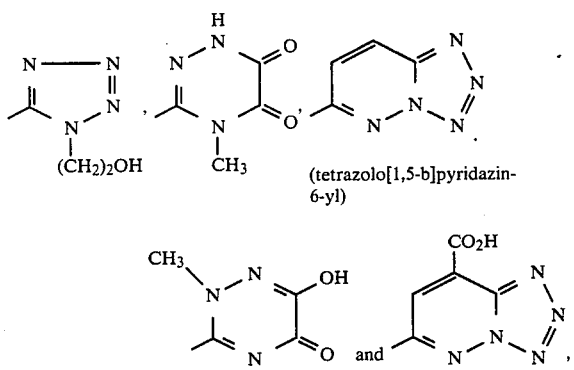

(tetrazolo[1,5-b]pyridazin-6-yl)

Typical examples of R are 4-thiazolyl, 1,2,3-thiadiazol-4-yl, 2-furyl, and 3-pyridyl.

$R^4$ is preferably $CH_3$, $C_2H_5$ or —$SO_2CH_3$.

$R^1$ is preferably

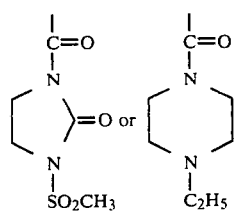

$R^2$ is preferably either (a) —$CH_2SHet$ where Het is an "individual group" as defined above, or (b) pyridiniummethyl.

The salts and esters (including in vivo hydrolysable esters) of the compounds of the formula (I) are well known to those skilled in the art. These salts include not only salts with —COOH, but also with —$OSO_2OH$ and —$SO_2OH$. The preferred salts are the sodium and potassium salts, and the triethylammonium salts. Some of the compounds may of course exist in zwitterionic form. The preferred in vivo hydrolysable esters are those of the formula: —$CH_2OCO^tBu$, —$CH_2OCOCH_3$, —$CH(CH_3)OCOCH_3$, —$CH(CH_3)OCOOEt$,

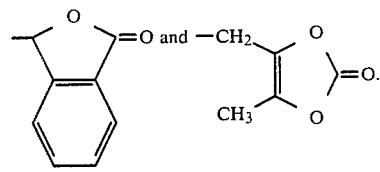

The preferred esters which are useful as intermediates are the t-butyl and benzhydryl esters.

In general, the DL- and D- forms at the starred carbon atom of the compounds of the formula (I) are preferred.

The compounds of the formula (I) are preferably prepared by the replacement of —$S.CH_3$ in the 7α-position with —NHOH. This can be done on the 7α-methylthio-7β-acylamino compounds, i.e., after acylation is carried out to introduce the group $RCH(NHR^1)CO$—, or on compounds not having the acyl group present in the 7β-position. The desired 3-substituent can be introduced before or after the hydroxyamino substituent is present. In addition any O- or carboxy-protecting groups can be removed before or after the —NHOH group is in position.

Typically, the hydroxyamino substituent is introduced by reacting the appropriate methylthio compound with a mercuric salt, e.g. mercuric trifluoroacetate, mercuric chloride or mercuric acetate, and preferably with mercuric acetate, at low temperature, e.g. —60° C., in a suitable organic solvent, eg dimethylformamide (DMF). Hydroxylamine hydrochloride again typically in DMF, is added, and the solution is slowly warmed to from —20° to +20° C. Hydroxylamine (preferably generated from hydroxylamine hydrochloride/triethylamine) can be used in place of hydroxylamine hydrochloride. The 7α-hydroxyamino product can then be isolated conventionally. $C_2$-$C_4$alkylthio, phenylthio or benzylthio derivatives can be used in place of the methylthio starting materials. Similarly metal salts (e.g. acetates) such as silver, thallium, lead or copper salts can be used in place of mercuric salts.

The 7α-methylthio compounds are either known compounds or can be prepared conventionally.

Typical routes to the compounds of the formula (I) are illustrated schematically as follows:
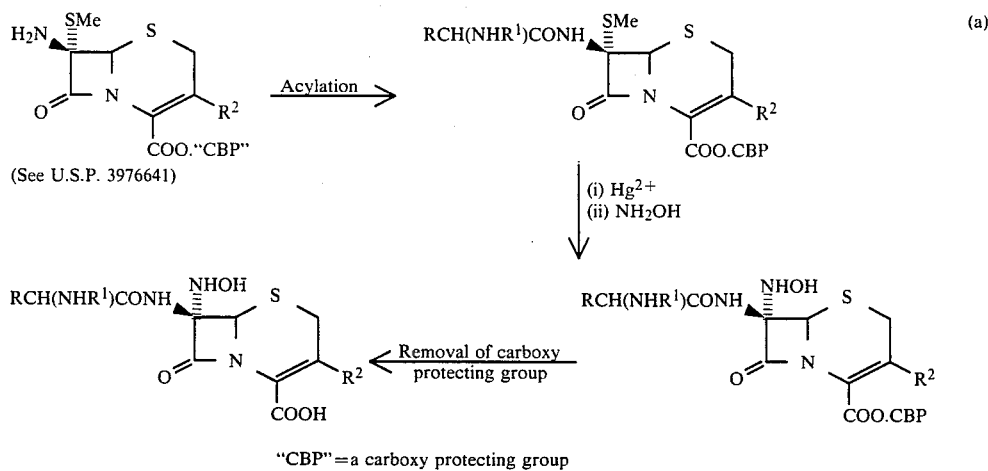
(See U.S.P. 3976641)
"CBP"=a carboxy protecting group
Modification at the 3-position (e.g. —CH₂OAc to —CH₂SHet) can if desired be carried out before or after introduction of the hydroxyamino substituent.
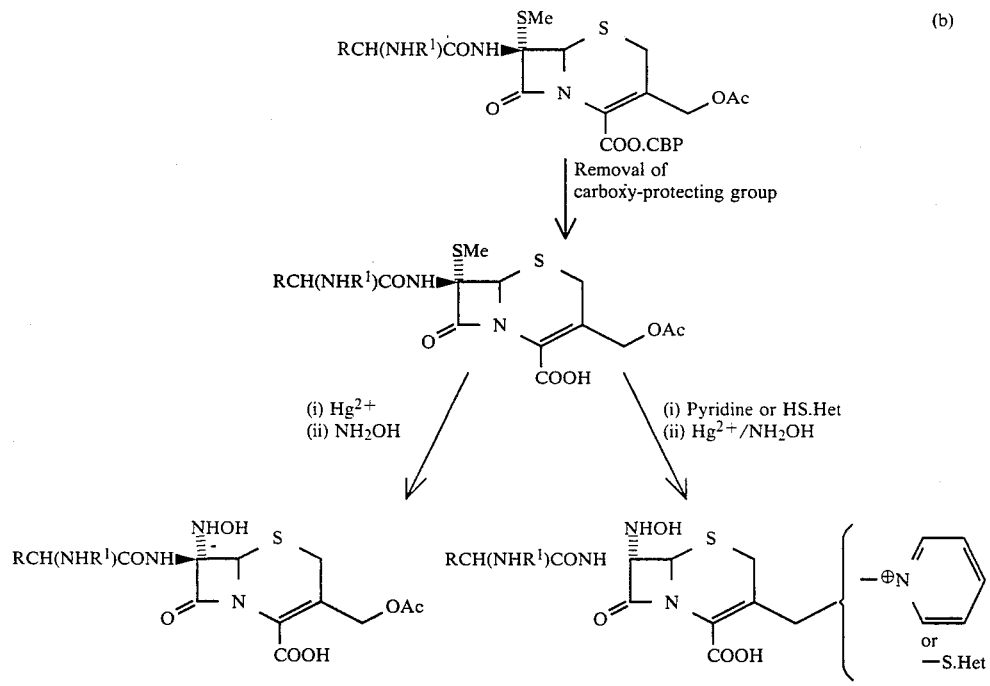
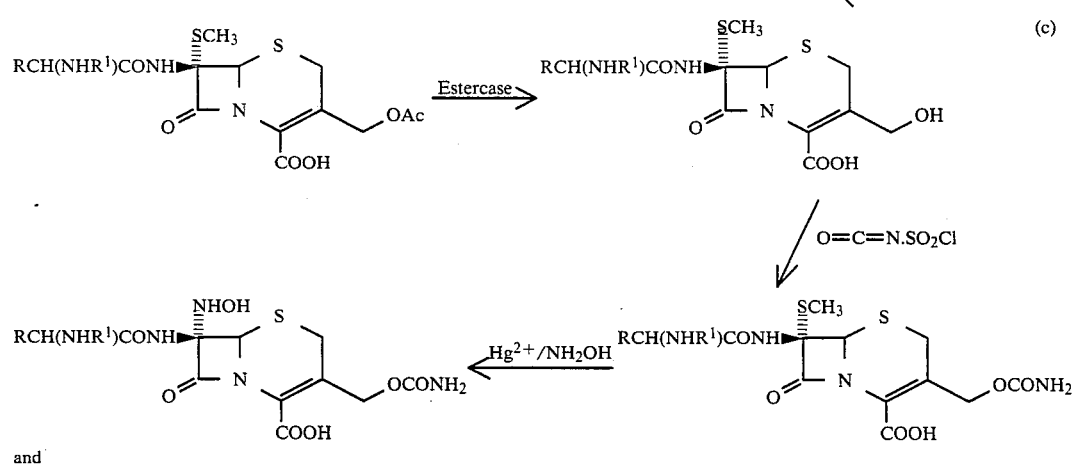
and

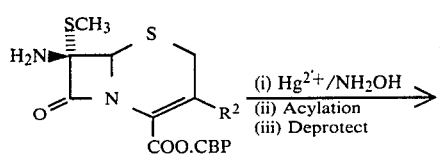 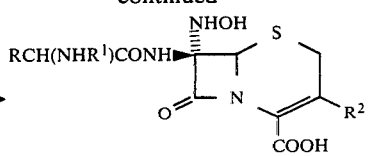

(see e.g. GB 1526793)

Any hydroxy-protecting groups, if present, can again be removed before or after insertion of the hydroxyamino group.

Apart from the insertion of the hydroxyamino group, all the above steps are conventional (see e.g. British patent application publication no. 2107307A or U.S. Pat. No. 4,297,488).

Acylation is typically carried out using an acid chloride or bromide of the acid $RCH(NHR^1)COOH$ or an O-protected derivative thereof. Alternatives are of course activated esters, mixed anhydrides. The reaction is typically carried out at low temperature ($-10°$ to $0°$ C.) in a suitable organic solent, eg dichloromethane. When an acid halide is used, the presence of an acid binding agent such as pyridine or triethylamine is preferred.

Many conventional carboxy protecting groups (CBP's) can be used, eg t-butyl, benzhydryl, benzyl, p-methoxybenzyl and p-nitrobenzyl. These can all be removed by conventional means. The preferred protecting groups are t-butyl, which is typically removed with trifluoroacetic acid, and benzhydryl, which is typically removed with anisole/$AlCl_3$ or anisole/trifluoroacetic acid.

Modifications at position 3 of the cephalosporin ring are carried out by conventional methods, e.g.:

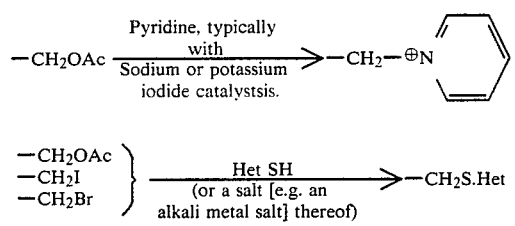

(Other suitable leaving groups than —OAc, I or Br can be used.)

The $C_3$ acetoxymethyl group can be reacted with the thiol in the presence of a Lewis acid such as boron trifluoride, if desired (see J5 5020 724).

It should be mentioned that derivatives of hydroxylamine protected on oxygen can be used in place of hydroxylamine in the formation of the —NHOH group, such derivatives including $H_2N$—$OSiMe_3$, $H_2N$—$OSiMe_2tBu$, $H_2N$—$OSiPh_2tBu$, $H_2N$—$OSi(C_1-C_4alkyl)_3$, $H_2N$—O.benzyl, $H_2N$—O.COO.benzyl, $H_2N$—O.COOtBu, $H_2N$—O.COOCH$_2$CCl$_3$, $H_2N$—O.COOCH$_2$CH=CH$_2$, $H_2N$—OCH$_2$CH=CH$_2$,

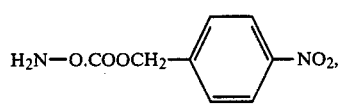

or $H_2N$—O.COOCH$_2$CH$_2$Si(CH$_3$)$_3$. The O-protecting groups can be removed conventionally.

The same O-protecting groups can be used, if desired, to protect the hydroxy groups of any hydroxy or hydroxyalkyl substituents. The preferred O-protecting groups are t-butyldiphenylsilyl and t-butyldimethylsilyl, removed with aqueous hydrofluoric acid.

The salts and in vivo hydrolysable esters can be prepared conventionally.

An alternative method of introducing hydroxyamino can be represented as follows:

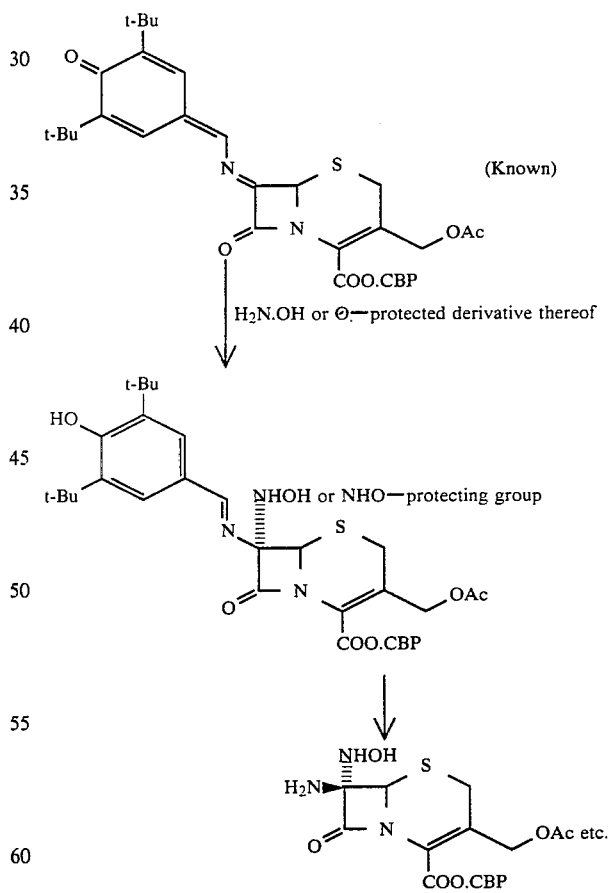

For administration to man in the curative or prophylactic treatment of bacterial infections, parenteral dosages of the compounds will typically be in the range of from 100 mg. to 8 g. daily for an average adult patient (70 kg), and, most commonly, for 1 g to 4 g daily. Thus for a typical adult patient, individual parenteral formulations will contain from 0.5 to 2 g. of active compound, in a suitable pharmaceutically acceptable vehicle. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered parenterally in admixture with a pharmaceutical diluent selected with regard to the intended route of administration and standard pharmaceutical practice. They can be injected intravenously, intramuscularly or subcutaneously. They are best used in the form of a sterile aqueous solution which may contain other substances, for example, enough salts or glucose to make the solution isotonic with blood, and the solution may also contain an anaesthetic such as lignocaine.

Thus in a further aspect the invention provides a pharmaceutical composition comprising a compound of the formula (I), or a pharmaceutically acceptable salt thereof, or in vivo hydrolysable ester thereof, together with a pharmaceutically acceptable diluent or carrier.

The compounds may also be administered in combination with other antibiotics and/or $\beta$-lactamase inhibitors such as sulbactam.

The invention also provides a compound of the formula (I), or a pharmaceutically acceptable salt or in vivo hydrolysable ester thereof, for use in medicine, in particular for use as an antibiotic.

The invention also provides a method of treating a bacterial infection in a human patient, which comprises administering to the patient an effective amount of a compound of the formula (I) or pharmaceutically acceptable salt or in vivo hydrolysable ester thereof.

The compounds of the formula (I) and their pharmaceutically acceptable salts and in vivo hydrolysable esters are antibiotics which have unexpectedly high activity. They are particularly active against gram negative organisms, such as *E. coli, Klebsiella pneumoniae, Proteus mirabilis, Proteus vulgaris, Proteus morganii, Providentia stuartii, Providentia rettgeri, Haemophilus influenzae* and *Bacteroides fragilis.*

The following Examples, in which all temperatures are in °C., illustrate the invention:

EXAMPLE 1

7α-Hydroxyamino-7β-[DL-2-(2-oxo-3-methylsulphonylimidazolidin-1-ylcarbonylamino)-2-(thiazol-4-yl)acetamido]cephalosporanic acid (a)
DL-2-[2-Oxo-3-methylsulphonylimidazolidin-1-ylcarbonylamino]-2-(thiazol-4-yl)acetic acid DL-2-Amino-2-(thiazol-4-yl)acetic acid (214 mg) [prepared by the method described in J. Med. Chem. 16, 978 (1973)] was taken up in water (10 ml) and the pH was adjusted to 6.5 by the addition of 2N sodium hydroxide solution. 2-Oxo-3-methylsulphonylimidazolidin-1-ylcarbonyl chloride (310 mg) was added to the stirred solution at room temperature in portions; the pH being maintained between 6.0 and 7.0 by the addition of 2N sodium hydroxide solution. When the addition was complete, the mixture was stirred for one hour, filtered, and the filtrate was washed with ethyl acetate (2×20 ml), acidified to pH 1.0, and extracted with ethyl acetate (2×20 ml). The combined extracts were washed with saturated sodium chloride solution (20 ml), dried (MgSO$_4$), filtered and evaporated to dryness in vacuo. The residue was triturated with methylene chloride and the solid product was separated by filtration to give the title compound as a white solid, (250 mg).

NMR (DMSO-d$_6$), $\delta$=3.34 (s, 3H); 3.77 (m, 4H); 5.59 (d, 1H, J=6 Hz); 7.79 (s, 1H); 8.76 (d, 1H, J=6 Hz); 9.09 (s, 1H).

(b) Benzhydryl
7α-methylthio-7β-[DL-2-(2-oxo-3-methylsulphonylimidazolidin-1-ylcarbonylamino)-2-(thiazol-4-yl)acetamido]cephalosporanate A suspension of DL-2-(2-oxo-3-methylsulphonylimidazolidin-1-ylcarbonylamino)-2-(thiazol-4-yl)acetic acid (600 mg) in methylene chloride (20 cm$^3$) stirred at 0° under nitrogen was treated with N-methylpiperidine (230 μl) in one portion to give a clear colourless solution. This solution was treated with ethyl chloroformate (200 μl) and the mixture stirred at 0° for thirty minutes to give a solution of the mixed anhydride. Benzhydryl 7β-amino-7α-methylthiocephalosporanate (1.01 g) in methylene chloride (10 cm$^3$) was added to the mixed anhydride solution at 0°, the solution was allowed to attain room temperature, stirred for 60 hours; washed successively with 0.2N hydrochloric acid (2×20 cm$^3$), saturated sodium hydrogen carbonate solution (2×20 cm$^3$) and saturated sodium chloride solution (20 cm$^3$), dried (MgSO$_4$), filtered and evaporated to dryness in vacuo. The residue was purified by medium-pressure flash-column chromatography on silica gel ("Merck" [Trade Mark] 230–400 mesh ASTM), eluting the product with 50% ethyl acetate/methylene chloride solution. The appropriate fractions were combined and evaporated to dryness in vacuo and re-stripped with 50% 1,1,1-trichloroethane/methylene chloride to give the title compound as a white solid, (1.1 g).

IR (CH$_2$Cl$_2$) 1784 cm$^{-1}$; 1738 cm$^{-1}$; 1691 cm$^{-1}$.

NMR (CDCl$_3$), $\delta$=1.92 and 1.94 (2×s, 3H); 2.05 and 2.23 (2×s, 3H); 3.31 and 3.35 (2×s, 3H); 3.77 (m, 4H); 4.7 (m, 2H); 5.09 and 5.10 (2×s, 1H); 5.84 (m, 1H); 6.87 (s, 1H); 7.30 (m, 10H); 7.71 and 7.72 (2×s, 1H); 8.85 (d, J=6 Hz, 1H); 9.07 and 9.08 (2×s, 1H); 9.63 (s, 1H).

(c)
7α-Methylthio-7β-[DL-2-(2-oxo-3-methylsulphonylimidazolidin-1-ylcarbonylamino)-2-(thiazol-4-yl)acetamido]cephalosporanic acid To a stirred solution of benzhydryl 7α-methylthio-7β-[DL-2-(2-oxo-3-methylsulphonylimidazolidin-1-ylcarbonylamino)-2-(thiazol-4-yl)acetamido]cephalosporanate (110 mg) in dichloromethane (15 cm$^3$) at room temperature was added anisole (293 μl) followed by trifluoroacetic acid (312 μl) and the mixture was stirred for 3 hours. The mixture was then evaporated to dryness and the residue was triturated with ether (50 ml) to give a pale yellow solid which, after rapid stirring for 2 hours, was separated by filtration, washed with ether and dried in vacuo to give the title compound, (80 mg).

IR (KBr disc) 1780 cm$^{-1}$; 1729 cm$^{-1}$; 1685 cm$^{-1}$.

NMR (DMSO-d$_6$) $\delta$=1.99 and 2.01 (2×s, 3H); 2.02 and 2.22 (2×s, 3H); 3.38 (s, 3H); 3.5 (m, 2H); 3.74 (m, 4H); 4.79 (m, 2H); 5.02 and 5.03 (2×s, 1H); 5.84 (m, 1H); 7.70 and 7.71 (2×s, 1H); 8.83 (m, 1H); 9.07 (s, 1H); 9.55 and 9.57 (2×s, 1H).

(d)
7α-Hydroxyamino-7β-[DL-2-(2-oxo-3-methylsulphonylimidazolidin-1-ylcarbonylamino)-2-(thiazol-4-yl)acetamido]cephalosporanic acid A solution of 7α-methylthio-7β-[DL-2-(2-oxo-3-methylsulphonylimidazolidin-1-ylcarbonylamio)-2-(1,3-thiazol-4-yl)acetamido]cephalosporanic acid (100 mg) in dimethylformamide (4 ml) stirred at −60° C. under nitrogen was treated successively with mercuric acetate (98 mg) in dimethylformamide (1 ml) and hydroxylamine hydrochloride (12 mg) in dimethylformamide (750 μl). The solution was then allowed to attain 0° over approximately one hour and added dropwise to dry diethyl ether (80 ml). After filtration, the ether-damp solid was suspended in methanol (20 ml) and saturated with hydrogen sulphide. The mixture was filtered and evaporated under vacuum. The residue was triturated with dichloromethane (50 ml) to give the title compound as a pale yellow solid, (62 mg).

IR (KBr) 1772 cm$^{-1}$; 1730 cm$^{-1}$; 1675 cm$^{-1}$.

NMR (DMSO-d$_6$), δ=2.01 (br, s, 3H); 3.37 (s, 3H); 3.79 (m, 4H); 4.78 (m, 2H); 5.07 (s, 1H); 5.89 (d, 1H, J=6 Hz); 7.67 (br s, 1H); 8.85 (m, 1H); 9.04 (br s, 1H); 9.19 (s, 1H); 10.32 (br, 1H).

EXAMPLE 2

7α-Hydroxyamino-7β-[DL-2-(2-oxo-3-methylsulphonylimidazolidin-1-ylcarbonylamino)-2-(thiazol-4-yl)acetamido]-3-[(tetrazolo[1,5-b]pyridazin-6-yl)-thiomethyl]ceph-3-em-4-carboxylic acid (a)
7α-Methylthio-7β-[DL-2-(2-oxo-3-methylsulphonylimidazolidin-1-ylcarbonylamino)-2(thiazol-4-yl)acetamido]-3-[(tetrazolo[1,5-b]pyridazin-6-yl)-thiomethyl]ceph-3-em-4-carboxylic acid 7α-Methylthio-7β-[DL-2-(2-oxo-3-methylsulphonylimidazolidin-1-ylcarbonylamino)-2-(thiazol-4-yl)acetamido]ceph-3-em-4-carboxylic acid [Example 1(c)] (100 mg) was dissolved in water (10 ml) containing sodium hydrogen carbonate (35 mg) then tetrazolo[1,5-b]pyridazine-6-thiol (35 mg) was added. The solution was warmed at 65° for 6 hours under a nitrogen atmosphere then cooled to room temperature, filtered, cooled in ice-water and acidified to pH2 with 2N hydrochloric acid. The precipitated solid was filtered, washed with water (10 ml) and dried under vacuum to yield the title compound, (40 mg).

IR (KBr) 1776 cm$^{-1}$; 1730 cm$^{-1}$; 1682 cm$^{-1}$.

NMR (DMSO-d$_6$), δ=2.00 and 2.21 (2×s, 3H); 3.34 (s, 3H); 3.60 (m, 3H); 3.77 (m, 4H); 4.13 and 4.60 (2×ABq, 2H); 4.99 and 5.00 (2×s, 1H); 5.82 (m, 1H); 7.72 (m, 2H); 8.57 (d, 1H, J=6 Hz); 8.82 (m, 1H); 9.05 and 9.07 (2×s, 1H); 9.56 (s, 1H).

(b)
7α-Hydroxyamino-7β-[DL-2-(2-oxo-3-methylsulphonylimidazolidin-1-ylcarbonylamino)-2-(thiazol-4-yl)acetamido]-3-[(tetrazolo[1,5-b]pyridazin-6-yl)thiomethyl]ceph-3-em-4-carboxylic acid The title compound (89 mg) was prepared from the 7α-methylthiocephem [Example 2(a)] (130 mg), mercuric acetate (112 mg) and hydroxylamine hydrochloride (15 mg) by the method described in Example 1(d).

IR (KBr) 1772 cm$^{-1}$; 1730 cm$^{-1}$; 1675 cm$^{-1}$.

NMR (DMSO-d$_6$), δ=3.35 (s, 3H); 3.45 (m, 2H); 3.77 (m, 4H); 4.10 and 4.59 (2×ABq, 2H); 5.00 and 5.02 (2×s, 1H); 5.86 (d, 1H, J=6 Hz); 7.73 (m, 2H); 8.57 (d, 1H, J=6 Hz); 8.82 (m, 2H); 9.03 and 9.06 (2×s, 1H); 9.39 (br, s, 1H); 10.28 (br, s, 1H).

EXAMPLE 3

7α-Hydroxyamino-7β-[DL-2-(2-oxo-3-methylsulphonylimidazolidin-1-ylcarbonylamino)-2-(1,2,3-thiadiazol-4-yl)acetamido]cephalosporanic acid (a) 2-Amino-2-(1,2,3-thiadiazol-4-yl)acetic acid hydrochloride A solution of 2-methoxyimino-2-(1,2,3-thiadiazol-4-yl)acetic acid (mixture of syn- and anti-isomers) (500 mg) [prepared by the method described in Belgian Pat. No. 859384 (1978)] in a mixture of methanol (10 cm$^3$) and water (2.3 cm$^3$) was treated with 1N hydrochloric acid (2.7 cm$^3$) and hydrogenated under 50 psi of hydrogen with 5% rhodium-on-charcoal (500 mg) for one hour. A further portion of catalyst (500 mg) was added and hydrogenation continued for one hour. After filtration the filtrate was evaporated to dryness in vacuo and the residue triturated with ether to give the title compound as an off-white solid, (490 mg).

NMR (DMSO-d$_6$); δ=4.98 (s, 1H); 7.43 (br, 4H); 9.12 (s, 1H).

(b)
DL-2-[2-oxo-3-methylsulphonylimidazolidin-1-ylcarbonylamino]-2-(1,2,3-thiadiazol-4-yl)acetic acid The title compound (1.3 g) was prepared from the amino acid of Example 3(a) (900 mg) and 2-oxo-3-methylsulphonylimidazolidin-1-ylcarbonyl chloride (1.04 g) by the method of Example 1(a).

NMR (DMSO-d$_6$) δ=3.34 (s, 3H); 3.76 (m, 4H); 6.02 (d, 1H, J=6 Hz); 8.96 (d, 1H, J=6 Hz); 9.26 (s, 1H).

(c) Benzhydryl
7α-Methylthio-7β-[DL-2-(2-oxo-3-methylsulphonylimidazolidin-1-ylcarbonylamino)-2-(1,2,3-thiadiazol-4-yl)acetamido]cephalosporanate The title compound (900 mg) was prepared from DL-2-[2-oxo-3-methylsulphonylimidazolidin-1-ylcarbonylamino]-2-(1,2,3-thiadiazol-4-yl)acetic acid (1.2 g), N-methylpiperidine (417 μl), ethyl chloroformate (327 μl) and benzhydryl 7β-amino-7α-methylthiocephalosporanate (1.66 g) by the method of Example 1(b).

IR (CH$_2$Cl$_2$) 1785 cm$^{-1}$; 1735 cm$^{-1}$; 1690 cm$^{-1}$.

NMR (CDCl$_3$) δ=2.04 (s, 3H); 2.27 and 2.30 (2×s, 3H); 3.34 (s, 3H); 3.35 (m, 2H); 3.94 (m, 4H); 4.91 and 4.94 (2×s, 1H); 4.93 and 5.12 (2×ABq, 2H); 6.36 (m, 1H); 6.91 (s, 1H); 7.40 (m, 10H); 7.76 and 7.86 (2×s, 1H); 8.72 (s, 1H); 9.21 (m, 1H).

(d)
7α-Methylthio-7β-[DL-2-(2-oxo-3-methylsulphonylimidazolidin-1-ylcarbonylamino)-2-(1,2,3-thiadiazol-4-yl)acetamido]cephalosporanic acid The title compound (603 mg) was prepared from its benzhydryl ester [Example 3(c)] (850 mg), trifluoroacetic acid (2 ml) and anisole (1 ml) by the method of Example 1(c).

IR (KBr) 1779 cm$^{-1}$; 1730 cm$^{-1}$; 1683 cm$^{-1}$.

NMR (DMSO-d$_6$) δ=1.99 and 2.01 (2×s, 3H); 2.03 and 2.23 (2×s, 3H); 3.35 (s, 3H); 3.42 (m, 2H); 3.72 (m, 4H); 4.68 and 4.90 (2×ABq, 2H); 5.05 and 5.06 (2×s, 1H); 6.18 (d, 1H, J=6 Hz); 9.02 (m, 1H); 9.14 and 9.16 (2×s, 1H); 9.80 and 9.83 (2×s, 1H).

(e)
7α-Hydroxyamino-7β-[DL-2-(2-oxo-3-methylsulphonylimidazolidin-1-ylcarbonylamino)-2-(1,2,3-thiadiazol-4-yl)acetamido]cephalosporanic acid The title compound (44 mg) was prepared from the 7α-methylthiocephem [Example 3(d)] (67 mg), mercuric acetate (66 mg) and hydroxylamine hydrochloride (8 mg) by the method of Example 1(d).

IR (KBr) 1780 cm$^{-1}$; 1728 cm$^{-1}$; 1680 cm$^{-1}$.

NMR (DMSO-d$_6$) δ=1.99 and 2.00 (2×s, 3H); 2.01 and 2.21 (2×s, 3H); 3.34 (s, 3H); 3.41 (m, 2H); 3.79 (m, 4H); 4.61 and 4.91 (2×ABq, 2H); 5.01 and 5.03 (2×s, 1H); 5.84 (m, 1H); 7.71 (br, s, 1H); 8.84 (m, 1H); 9.03 and 9.04 (2×s, 1H); 9.39 and 9.60 (2×s, 1H); 10.24 (s, 1H).

EXAMPLE 4

3-[(5,6-Dioxo-4-methyl-1,4,5,6-tetrahydro-1,2,4-triazin-3-yl)thiomethyl]-7α-hydroxyamino-7β-[DL-2-(2-oxo-3-methylsulphonylimidazolidin-1-ylcarbonylamino)-2-(1,2,3-thiadiazol-4-yl)acetamido]ceph-3-em-4-carboxylic acid (a)
3-[5,6-Dioxo-4-methyl-1,4,5,6-tetrahydro-1,2,4-triazin-3-yl)thiomethyl]-7α-methylthio-7β-[DL-2-(2-oxo-3-methylsulphonylimidazolidin-1-ylcarbonylamino)-2-(1,2,3-thiadiazol-4-yl)acetamido]ceph-3-em-4-carboxylic acid A solution of 7α-methylthio-7β-[DL-2-(2-oxo-3-methylsulphonylimidazolidin-1-ylcarbonylamino)-2-(1,2,3-thiadiazol-4-yl)acetamido]cephalosporanic acid [Example 3(d)] (220 mg) and 5,6-dioxo-4-methyl-1,4,5,6-tetrahydro-1,2,4-triazinyl-3-thiol (81 mg) in 1,2-dichloroethane (70 cm$^3$) was refluxed under nitrogen for 14 hours. The mixture was cooled to room temperature and the title compound filtered and dried in vacuo, (170 mg).

IR (KBr) 1777 cm$^{-1}$, 1732 cm$^{-1}$, 1680 cm$^{-1}$.

NMR (DMSO-d$_6$), δ=2.03 and 2.23 (2×s, 3H); 3.24 and 3.26 (2×s, 3H); 3.35 (s, 3H); 3.52 (m, 2H); 3.75 (m, 4H); 3.82 and 4.12 (2×ABq, 2H); 5.02 and 5.03 (2×s, 1H); 6.18 (d, 1H, J=6 Hz); 9.02 (m, 1H); 9.13 and 9.16 (2×s, 1H); 9.80 and 9.83 (2×s, 1H).

(b)
3-[(5,6-Dioxo-4-methyl-1,4,5,6-tetrahydro-1,2,4-triazin-3-yl)thiomethyl]-7α-hydroxyamino-7β-[DL-2-(2-oxo-3-methylsulphonylimidazolidin-1-ylcarbonylamino)-2-(1,2,3-thiadiazol-4-yl)acetamido]ceph-3-em-4-carboxylic acid The title compound (96 mg) was prepared from the 7α-methylthiocephem [Example 4(a)] (158 mg), mercuric acetate (135 mg) and hydroxylamine hydrochloride (16 mg) by the method of Example 1(d).

IR (KBr) 1772 cm$^{-1}$; 1727 cm$^{-1}$; 1700 cm$^{-1}$.

NMR (DMSO-d$_6$), δ=3.24 and 3.26 (2×s, 3H); 3.35 (s, 3H); 3.51 (m, 2H); 3.76 (m, 4H); 3.90 and 4.1 (2×ABq, 2H); 4.99 and 5.00 (2×s, 1H); 6.21 (m, 1H); 8.97, 9.00, 9.04 and 9.07 (2×d, 1H, J=6 Hz); 9.14 and 9.17 (2×s, 1H); 9.46 and 9.62 (2×s, 1H); 10.24 l (s, 1H).

EXAMPLE 5

7α-Hydroxyamino-7β-[DL-2-(2-oxo-3-methylsulphonylimidazol-1-ylcarbonylamino)-2-(1,2,3-thiadiazol-4-yl)acetamido]-3-(pyridiniummethyl)ceph-3-em-4-carboxylate (a)
7α-Methylthio-7β-[DL-2-(2-oxo-3-methylsulphonylimidazolidin-1-ylcarbonylamino)-2-(1,2,3-thiadiazol-4-yl)acetamido]-3-(pyridiniummethyl)ceph-3-em-4-carboxylate 7α-Methylthio-7β-[DL-2-(2-oxo-3-methylsulphonylimidazolidin-1-ylcarbonylamino)-2-(1,2,3-thiadiazol-4-yl)acetamido]cephalosporanic acid [Example 3(d)] (500 mg) was dissolved in water (20 ml) containing sodium hydrogen carbonate (71 mg) then potassium iodide (1.92 g) and pyridine (374 μl) were added. The solution was heated at 70° for 4 hours, cooled, and concentrated in vacuo to 5 ml. This concentrate was diluted with acetone (50 ml) and chromatographed over silica (75 g), eluting with acetone:water (3:1) to afford the crude title compound. This material was dissolved iln water (5 ml), filtered through "Hyflo" [Trade Mark] and freeze dried to afford the pure title compound, (110 mg).

IR (KBr) 1780 cm$^{-1}$; 1730 cm$^{-1}$; 1656 cm$^{-1}$.

NMR (DMSO-d$_6$), δ=1.96 and 2.25 (2×s, 3H); 2.88 and 3.43 (2×m, 2H); 3.33 and 3.34 (2×s, 3H); 3.76 (m, 4H); 4.92 and 4.96 (2×s, 1H); 5.08 and 5.58 (2×ABq, 2H); 6.15 (m, 1H); 8.14 (m, 2H); 8.56 (m, 1H); 9.00 (m, 1H); 9.09 and 9.14 (2×s, 1H); 9.35 and 9.43 (2×d, 1H, J=6 Hz); 9.74 and 9.75 (2×s, 1H).

(b)
7α-Hydroxyamino-7β-[DL-2-(2-oxo-3-methylsulphonylimidazolidin-1-ylcarbonylamino)-2-(1,2,3-thiadiazol-4-yl)acetamido]-3-(pyridiniummethyl)ceph-3-em-4-carboxylate The title compound (67 mg) was prepared from the 7α-methylthiocephem [Example 5(a)] (78 mg), mercuric acetate (75 mg) and hydroxylamine hydrochloride (9 mg) by the method of Example 1(d).

IR (KBr) 1777 cm$^{-1}$; 1735 cm$^{-1}$; 1657 cm$^{-1}$.

NMR (DMSO-d$_6$) δ=3.35 and 3.36 (2×s, 3H); 3.40 (m, 2H); 3.79 (m, 4H); 5.08 (s, 1H); 5.09 and 5.47 (2×ABq, 2H); 6.21 (d, 1H, J=6 Hz); 8.21 (m, 2H); 8.63 (m, 2H); 9.05 (m, 3H); 9.17 and 9.22 (2×s, 1H); 9.54 and 9.66 (2×s, 1H).

EXAMPLE 6

7β-[DL-2-(4-Ethyl-2,3-dioxopiperazin-1-ylcarbonylamino)-2-(1,2,3-thiadiazol-4-yl)acetamido]-7α-hydroxyamino-3-[(1-{2-hydroxyethyl}-1H-tetrazol-5-yl)thiomethyl]ceph-3-em-4-carboxylic acid (a)
DL-2-(4-Ethyl-2,3-dioxopiperazin-1-ylcarbonylamino)-2-(1,2,3-thiadiazol-4-yl)acetic acid The title compound (1.24 g) was prepared from 2-amino-2-(1,2,3-thiadiazol-4-yl)acetic acid hydrochloride [Example 3(a)] (912 mg) and 4-ethyl-2,3-dioxopiperazin-1-ylcarbonyl chloride (953 mg) by the method of Example 1(a).

NMR (DMSO-d$_6$) δ=1.06 (t, 3H, J=7 Hz); 3.37 (q, 2H, J=7 Hz); 3.56 (m, 2H); 3.94 (m, 2H); 6.04 (d, 2H, J=6 Hz); 9.26 (s, 1H); 10.01 (d, 1H, J=6 Hz).

(b) Benzhydryl 7β-[DL-2-(4-ethyl-2,3-dioxopiperazin-1-ylcarbonylamino)-2-(1,2,3-thiadiazol-4-yl)acetamido]-7α-methylthiocephalosporanate The title compound (130 g) was prepared from DL-2-(4-ethyl-2,3-dioxopiperazin-1-ylcarbonylamino)-2-(1,2,3-thiadiazol-4-yl)acetic acid [Example 6(a)] (1.20 g), N-methylpiperidine (445 μl) ethyl chloroformate (384 μl) and benzhydryl 7β-amino-7α-methylthiocephalosporanate (1.95 g) by the method of Example 1(b).

IR ($CH_2Cl_2$) 1780 $cm^{-1}$, 1710 $cm^{-1}$, 1670 $cm^{-1}$.

NMR (DMSO-$d_6$), δ=1.23 (t, 3H, J=6 Hz); 2.04 (s, 3H); 2.27 and 2.28 (2×s, 3H); 3.34 (s, 2H); 3.56 (m, 4H); 4.10 (m, 2H); 4.91 and 4.95 (2×s, 1H); 4.93 and 5.11 (2×ABq, 2H); 6.38 (m, 1H); 6.89 (s, 1H); 7.40 (m, 10H); 806 and 8.68 (2×s, 1H); 8.81 and 8.82 (2×s, 1H); 10.16 (m, 1H).

(c) 7β-[DL-2-(4-Ethyl-2,3-dioxopiperazin-1-ylcarbonylamino)-2-(1,2,3-thiadiazol-4-yl)acetamido]-7α-methylthiocephalosporanic acid The title compound (594 mg) was prepared from the benzhydryl ester of Part (b) (1.25 g) by the method of Example 1(c).

IR (KBr) 1780 $cm^{-1}$, 1710 $cm^{-1}$, 1678 $cm^{-1}$.

NMR (DMSO-$d_6$), δ=1.07 (t, 3H, J=6 Hz); 1.99 and 2.01 (2×s, 3H); 2.03 and 2.24 (2×s, 3H); 3.30 (m, 4H); 3.55 (m, 2H); 3.90 (m, 2H); 4.64 and 4.91 (2×ABq, 2H); 5.06 and 5.07 (2×s, 1H); 6.21 (m, 2H); 9.13 and 9.15 (2×s, 1H); 9.84 (br s, 1H); 10.05 (m, 1H).

(d) 7β-[DL-2-(4-Ethyl-2,3-dioxopiperazin-1-ylcarbonylamino)-2-(1,2,3-thiadiazol-4-yl)acetamido]-3[(1-{2-hydroxyethyl}-1H-tetrazol-5-yl)thiomethyl]-7α-methylthiocephalosporanic acid The title compound (100 mg) was prepared from 7β-[DL-2-(4-ethyl-2,3-dioxopiperazin-1-ylcarbonylamino)-2-(1,2,3-thiadiazol-4-yl)acetamido]-7α-methylthiocephalosporanic acid [Example 6(c)] (100 mg) and 1-(2-hydroxyethyl)-1H-tetrazole-5-thiol (46 mg) by the method of Example 4(a).

IR (KBr) 1778 $cm^{-1}$, 1711 $cm^{-1}$, 1672 $cm^{-1}$.

NMR (DMSO-$d_6$) δ=1.06 (t, 3H, J=6 Hz); 2.01 and 2.23 (2×s, 3H); 3.37 (m, 4H); 3.56 (m, 2H); 3.78 (m, 4H); 4.15 and 4.44 (2×ABq, 2H); 4.24 (m, 2H); 5.00 and 5.01 (2×s, 1H); 5.02 (br, 1H); 6.21 (d, 1H, J=6 Hz); 9.12 and 9.15 (2×s, 1H); 9.82 and 9.84 (2×s, 1H); 10.07 (m, 1H).

(e) 7β-[DL-2-(4-Ethyl-2,3-dioxopiperazin-1-ylcarbonylamino)-2-(1,2,3-thiadiazol-4-yl)acetamido]-7α-hydroxyamino-3-[(1-(2-hydroxyethyl)-1H-tetrazol-5-yl)thiomethyl]ceph-3-em-4-carboxylic acid The title compound (55 mg) was prepared from the 7α-methylthiocephem [Example 6(d)] (75 mg), mercuric acetate (67 mg) and hydroxylamine hydrochloride (11 mg) by the method of Example 1(d).

IR (KBr) 1775 $cm^{-1}$, 1710 $cm^{-1}$, 1670 $cm^{-1}$.

NMR (DMSO-$d_6$), δ=1.06 (t, 3H, J=6 Hz); 3.54 (m, 10H); 4.10 and 4.36 (2×ABq, 2H); 4.21 (m, 2H); 4.96 and 4.97 (2×s, 1H); 6.24 (m, 1H); 9.14 and 9.16 (2×s, 1H); 9.47 and 9.62 (2×s, 1H); 10.04 (m, 1H); 10.25 (s, 1H).

The following compounds of the formula (I) were prepared from the appropriate starting materials using the methods described above. The side chains all have DL-stereochemistry:

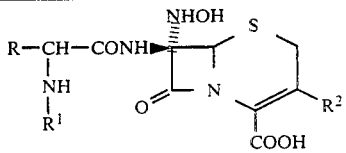

| Example No. | Preparation as for Example No. | R | $R^1$ | $R^2$ | IR (KBr) $cm^{-1}$ | NMR (DMSO—$d_6$) δ = |
|---|---|---|---|---|---|---|
| 7 | 2(a)–(b) | thiadiazolyl | piperazinedione with SO₂CH₃ | $-CH_2S-$ tetrazolopyridazine | 1776, 1729, 1685 | 3.34 (s, 3H); 3.35 (m, 2H); 3.78 (m, 4H); 4.15 and 4.56 (2 × ABq, 2H); 5.00 and 5.01 (2 × s, 1H); 6.21 (m, 1H); 7.73 (m, 1H); 8.98 (d, 1H, J = 6 Hz); 8.98 and 9.05 (2 × d, 1H, J = 6Hz); 9.14 and 9.16 (2 × s, 1H); 9.44 and 9.62 (2 × s, 1H). |
| 8 | 4(a)–(b) | thiadiazolyl | ethyl-dioxopiperazinyl | $-CH_2S-$ N-methyl-thiadiazolinone | 1776, 1708, 1676 | 1.06 (t, 3H, J = 7Hz); 3.25 and 3.26 (2 × s, 3H); 3.36 (m, 4H); 3.55 (m, 2H); 3.89 (m, 2H); 3.90 and 4.11 (2 × ABq, 2H); 4.99 and 5.02 (2 × s, 1H); 6.24 (m, 1H); 9.14 and 9.16 (2 × s, 1H); 9.49 and 9.63 (2 × s, 1H); 10.03 (m, 1H); 10.24 (s, 1H). |

| Example No. | Preparation as for Example No. | R | R¹ | R² | IR (KBr) cm⁻¹ | NMR (DMSO—d₆) δ = |
|---|---|---|---|---|---|---|
| 9 | 4(a)–(b) | (4-methyl-1,2,3-thiadiazol-5-yl) | $-\overset{|}{\underset{SO_2CH_3}{N}}-C(=O)-N(-CH_2CH_2-)C(=O)$ (3-methylsulfonyl-2-oxoimidazolidin-1-yl-carbonyl) | $-CH_2S-$(1-(2-hydroxyethyl)tetrazol-5-yl); (CH₂)₂OH | 1780, 1727, 1680 | 3.35 (s, 3H); 3.63 (m, 2H); 3.74 (m, 6H); 4.11 and 4.37 (2 × ABq, 2H); 4.30 (m, 2H); 4.96 (s, 1H); 4.97 (br, 1H); 6.22 (m, 1H); 8.99 and 9.05 (2 × d, 1H, J = 6Hz); 9.14 and 9.17 (2 × s, 1H); 9.44 and 9.61 (2 × s, 1H); 10.24 (s, 1H). |
| 10 | 2(a)–(b) | (4-methyl-1,2,3-thiadiazol-5-yl) | (3-methylsulfonyl-2-oxoimidazolidin-1-ylcarbonyl) | $-CH_2S-$(tetrazolo[1,5-b]pyridazine-6-carboxylic acid); CO₂H | 1777, 1731, 1690 | 3.36 (s, 3H); 3.50 (m, 6H); 4.41 and 4.62 (2 × ABq, 2H); 4.99 and 5.01 (2 × s, 1H); 6.23 (m, 1H); 7.89 (s, 1H); 8.10 and 8.18 (2 × s, 1H); 8.98 and 9.06 (2 × d, 1H, J = 6Hz); 9.14 and 9.17 (2 × s, 1H); 9.46 and 9.62 (2 × s, 1H). |
| 11 | 2(a)–(b) | (4-methyl-1,2,3-thiadiazol-5-yl) | (4-ethyl-2,3-dioxopiperazin-1-ylcarbonyl) | $-CH_2S-$(tetrazolo[1,5-b]pyridazine-6-carboxylic acid); CO₂H | 1775, 1710, 1675, 1640 | 1.06 (m, 3H); 3.50 (m, 8H); 4.11 and 4.58 (2 × ABq, 2H); 5.01 and 5.03 (2 × s, 1H); 6.23 (m, 22H); 7.95 (s, 1H); 9.00 (s, 1H); 9.18 and 9.19 (2 × s, 1H); 9.51 and 9.61 (2 × s, 1H); 10.06 (m, 1H). |

EXAMPLE 12

3-Acetoxymethyl-7β-[DL-2-furyl-2-(3-methylsulphonyl-2-oxo-imidazolidin-1-ylcarbonylamino)acetamido]-7α-hydroxyaminoceph-3-em-4-carboxylic acid (a)
DL-2-furyl-2-(3-methylsulphonyl-2-oxoimidazolidin-1-ylcarbonylamino)acetic acid The title compound was prepared from DL-2-amino-2-(2-furyl)acetic acid [J. Antibiotics 31 (6), 546 (1978)] by the method of Example 1(a).

NMR (CDCl₃), δ=3.36 (s, 3H); 3.82–4.05 (m, 4H); 5.71 (d, J=6, 1H); 6.39 (m, 1H); 6.45 (m, 1H); 7.42 (s, 1H); 8.69 (d, J=6, 1H).

(b)
Benzhydryl-3-acetoxymethyl-7β-[DL-2-furyl-2-(3-methylsulphonyl-2-oxoimidazolidin-1-ylcarbonylamino)acetamido]-7α-methylthioceph-3-em-4-carboxylate A suspension of DL-2-furyl-2-(3-methylsulphonyl-2-oxoimidazolidin-1-ylcarbonylamino)acetic acid (0.97 g) in dichloromethane (25 ml) was treated with pyridine (240 μl). After stirring at room temperature for 5 minutes the almost clear solution was cooled to −30° and trichloroacetyl chloride (330 μl) was added. The solution was stirred at −30° for 1 hour. A solution of benzhydryl 7β-amino-7α-methylthiocephalosporanate (1.60 g) in dichloro-methane (20 ml) was added and the reaction mixture warmed to room temperature over 1 hour. Ethyl acetate (100 ml) was added and the mixture washed with 1N hydrochloric acid (2×50 ml) and brine (50 ml). Drying, followed by evaporation of the solvent in vacuo gave the crude product which after chromatography on silica gel (eluting with a dichloromethane-ethyl acetate gradient) afforded the title compound as a yellow solid, (0.45 g).

IR (KBr) 1785 cm⁻¹.

NMR (CDCl₃), δ=2.08 and 2.12 (2×s, 3H); 2.24 and 2.32 (2×s, 3H); 3.24–3.58 (m, 2H); 3.82–4.06 (m, 4H); 4.92 and 5.16, 4.94 and 5.16 (2×ABq, J=14, 2H); 4.96 and 4.98 (2×s, 1H); 5.78 and 5.81 (2×d, J=6, 1H); 6.41 (m, 1H); 6.55 (m, 1H); 6.95 and 6.97 (2×s, 1H); 7.19–7.57 (m, 11H); 8.81 and 8.82 (2×d, J=6, 1H).

(c)
3-Acetoxymethyl-7β-[DL-2-furyl-2-(3-methylsulphonyl-2-oxoimidazolidin-1-ylcarbonylamino)acetamido]-7α-methylthioceph-3-em-4-carboxylic acid To a solution of benzhydryl 3-acetoxymethyl-7β-[DL-2-furyl-2-(3-methylsulphonyl-2-oxoimidazolidin-1-ylcarbonylamino)acetamido]-7α-methylthioceph-3-em-4-carboxylate (0.45 g) in dichloromethane (25 ml) at −65° under nitrogen was added anisole (0.36 g) followed by a solution of aluminum chloride (0.224 g) in nitromethane (2 ml) with stirring. After 5 minutes, ethyl acetate (10 ml) and 1N hydrochloric acid (15 ml) was added and stirring continued for 15 minutes to room temperature. The ethyl acetate layer was separated and dried. Evaporation gave a yellow residue which on trituration with ether gave the product as a yellow solid, (0.315 g).

IR (KBr) 1785 cm$^{-1}$.

NMR (DMSO-d$_6$), δ=2.02 and 2.04 (2×s, 3H); 2.12 and 2.23 (2×s, 3H); 3.38 (s, 3H); 3.38–3.67 (m, 2H); 3.69–3.92 (m, 4H); 4.67 and 4.96, 4.69 and 5.01 (2×ABq, J=14, 2H); 5.10 and 5.12 (2×s, 1H); 5.80 (d, J=6); 6.43 (m, 2H); 7.66 (m, 1H); 8.59 and 8.63 (2×d, J=6, 1H); 9.68 (d, J=6, 1H).

(d)

3-Acetoxymethyl-7β-[DL-2-furyl-2-(3-methylsulphonyl-2-oxoimidazolidin-1-ylcarbonylamino)acetamido]-7α-hydroxyaminoceph-3-em-4-carboxylic acid The title compound was prepared from the product of part (c) by the method of Example 1(d).

IR (KBr) 1785 cm$^{-1}$.

NMR (DMSO-d$_6$), δ=2.01 and 2.03 (2×s, 3H); 3.38 (s, 3H); 3.37–3.62 (m, 2H); 3.70–3.91 (m, 4H); 4.61 and 4.92, 4.63 and 4.96 (2×ABq, J=14, 2H); 5.06 (s, 1H); 5.81 (d, J=6, 1H); 6.36–6.59 (m, 3H); 7.61 (m, 1H); 8.16 and 8.18 (2×s, 1H); 8.58 and 8.62 (2×d, J=6, 1H); 9.37 and 9.46 (2×s, 1H).

EXAMPLE 13

3-Acetoxymethyl-7β-[DL-2-(2-oxo-3-methylsulphonylimidazolidin-1-ylcarbonylamino)-2-(3-pyridyl)acetamido]-7α-hydroxyaminoceph-3-em-4-carboxylic acid (a)

DL-2-(2-oxo-3-methylsulphonylimidazolidin)-1-ylcarbonylamino)-2-(3-pyridyl)acetic acid The title compound was prepared from DL-3-pyridylglycine [prepared similarly to the method of Davis et al for 4-pyridylglycine, Arch. Biochem. Biophys. 87, 88 (1960)]. by the method of Example 1(a).

NMR (DMSO-d$_6$) δ=3.34 (s, 3H); 3.70 (m, 4H); 4.78 (d, J=6 Hz, 1H); 7.27 (m, 1H); 7.62 (d, J=6 Hz, 1H); 8.35 (d, J=3 Hz, 1H); 8.49 (s, 1H); 9.00 (d, J=6 Hz, 1H).

(b) Benzhydryl 3-acetoxymethyl-7β-[DL-2-(2-oxo-3-methylsulphonylimidazolidin-1-ylcarbonylamino)-2-(3-pyridyl)acetamido]-7α-methylthioceph-3-em-4-carboxylate The pridylacetic acid (0.55 g) from Example 13(a) was sonicated with pyridine (0.13 ml) in acetonitrile (10 ml) for 0.5 hours. The suspension was cooled to −40° C., trichloroacetyl chloride (0.215 ml) was added and the mixture was stirred for 2 hours at −40° C. Benzhydryl 3-acetoxymethyl-7β-amino-7α-methylthio-ceph-3-em-4-carboxylate (0.935 g) in acetonitrile (10 ml) was then added, and the reaction mixture was warmed to 20° C. and stirred overnight. The solvent was removed in vacuo, the residue dissolved in methylene chloride (20 ml) and washed with aqueous sodium bicarbonate (2×20 ml). The organic phase was dried over magnesium sulphate and the solvent removed in vacuo. The residue was chromatographed (silica gel, ethyl acetate:isopropanol, 95:5) to give the title compound, (0.26 g).

IR (KBr), 1785 cm$^{-1}$.

NMR (DMSO-d$_6$) δ=1.91, 1.94, 1.97 and 2.21 (4×s, 6H); 3.27 (s, 3H); 3.48 and 3.60 (ABq, J=14 Hz, 2H); 3.70 (m, 4H); 4.60, 4.67 and 4.48, 4.90 (2×ABq, J=12 Hz, 2H); 5.14 and 5.15 (2×s, 1H); 4.63 (m, 1H); 6.87 (s, 1H); 7.36 (m, 12H); 7.77 (m, 1H); 8.50 (m, 1H); 8.65 (s, 1H); 8.83 (2×d, J=6 Hz, 1H); 9.82 and 9.87 (2×s, 1H).

(c)

3-Acetoxymethyl-7β-[DL-2-(2-oxo-3-methylsulphonylimidazolidin-1-ylcarbonylamino)-2-(3-pyridyl)acetamido]-7α-methylthioceph-3-em-4-carboxylic acid The benzhydryl ester (0.25 g) from Example 13(b) above in methylene chloride (10 ml) at −20° C. was treated with anisole (0.27 ml) followed by trifluoroacetic acid (1 ml). The reaction mixture was warmed to 20° C. and stirred for 1 hour. The solvent was then removed in vacuo and the residue dissolved in methanol (15 ml). Isopropyl alcohol (10 ml) was added and the methanol was removed in vacuo. The solid was filtered off, washed with ether (2×20 ml) and dried in vacuo, yielding the title compound as an off white solid, (0.16 g).

IR (KBr) 1780 cm$^{-1}$.

NMR (DMSO-d$_6$) δ=1.95, 1.98, 2.01 and 2.21 (4×s, 6H); 3.34 (s, 3H); 3.50 (m, 2H); 3.70 (m, 4H); 4.60, 4.66 and 4.92, 5.04 (2×ABq, J=12 Hz, 2H); 5.07 and 5.08 (2×s, 1H); 5.64 (d, J=6 Hz, 1H); 7.47 (m, 1H); 7.84 (m, 1H); 8.55 (m, 1H); 8.67 (s, 1H); 8.82, 8.86 (2×d, J=6 Hz, 1H); 9.77 and 9.82 (2×s, 1H).

(d)

3-Acetoxymethyl-7β-[DL-2-(2-oxo-3-methylsulphonylimidazolidin-1-ylcarbonylamino)-2-(3-pyridyl)acetamido]-7α-hydroxyamino-ceph-3-em-4-carboxylic acid (i) The 7α-methylthio cephem (0.14 g) from Example 13(c) in dimethylformamide (3 ml) was treated with mercuric acetate (0.076 g) in DMF (1 ml) at −60° C. followed by O-tert-butyldiphenylsilylhydroxylamine (0.71 g) in dimethylformamide (1 ml). The reaction mixture was warmed to −5° C. and stirred at −5° C. for 1 hour. The reaction mixture was diluted with ethyl acetate:THF (2:1, 90 ml) and washed with brine (3×50 ml). The organic phase was dried over magnesium sulphate and the solvents removed in vacuo yielding 3-acetoxymethyl-7β-[DL-2-(2-oxo-3-methylsulphonylimidazolidin-1-ylcarbonylamino)-2-(3-pyridyl)acetamido]-7α-O-tert-butyldiphenylsilylhydroxyamino-ceph-3-em-4-carboxylate, (0.145 g).

(ii) The 7α-tert-butyldiphenylsilylhydroxyamino-cephalosporanate (0.14 g) from Example 13(d)(i) in acetonitrile/tetrahydrofuran (1:1) (4 ml) was treated with 40% hydrofluoric acid at 0° C. for 0.5 hours. The solvents were removed under high vacuum and the residue dissolved in methanol (10 ml), filtered, isopropyl alcohol (10 ml) was added and the methanol removed in vacuo. The solid was filtered and washed with ether (2×20 ml) yielding the title compound (0.08 g) as the hydrofluoride salt.

IR (KBr), 1785 cm$^{-1}$.

NMR (DMSO-d$_6$), δ=2.00 and 2.04 (2×s, 3H); 3.34 (s, 3H); 3.50 (m, 2H); 3.70 (m, 4H); 4.58 and 4.90 (2×ABq, 2H); 4.97 and 4.99 (2×s, 1H); 5.02 (s, 1H); 5.76 (m, 1H); 7.82 (m, 1H); 8.23 (m, 1H); 8.74 (br, 1H); 8.82 (br, 1H); 8.92 (m, 1H); 9.64 (m, 1H).

EXAMPLE 14

7β-[DL-2-(2-oxo-3-methylsulphonylimidazolidin-1-ylcaronylamino)-2-(3-pyridyl)acetamido]-7α-hydroxyamino-3-(pyridiniummethyl)ceph-3-em-4-carboxylate (a)

7β-[DL-2-(2-oxo-3-methylsulphonylimidazolidin-1-ylcarbonylamino)-2-(3-pyridylacetamido)-7α-methylthio-3-(pyridiniummethyl)ceph-3-em-4-carboxylate The title compound was prepared from the product of Example 13(c) by the method of Example 5(a).

IR (KBr) 1765 cm$^{-1}$.

NMR (DMSO-d$_6$) δ=1.86 and 2.23 (2×s, 3H); 3.34 (s, 3H); 3.50 (m, 2H); 3.70 (m, 4H); 4.95 and 4.98 (2×s, 1H); 5.12 (m, 1H); 5.60 (m, 2H); 7.36 (m, 1H); 7.73 (m, 1H); 8.13 (m, 2H); 8.4–8.62 (m, 4H); 8.80 (m, 1H); 9.34 and 9.42 (2 d, J=4 Hz, 1H); 9.73 (s, 1H).

(b)

7β-[DL-2-(2-oxo-3-methylsulphonylimidazolidin-1-ylcarbonylamino)-2-(3-pyridyl)acetamido]7α-hydroxyamino-3-(pyridiniummethyl)ceph-3-em-4-carboxylate The 7α-methylthiocephem (0.12 g) from Example 14(a) was dissolved in dimethylformamide (3 ml) and cooled to −60° C. A solution of mercuric acetate (0.064 g) in dimethylformamide (1 ml) followed by hydroxylamine hydrochloride (0.015 g) in dimethylformamide (1 ml) and triethylamine (0.025 ml) were added. The reaction was stirred at −5° C. for 2 hours, diluted with acetone (50 ml) and chromatographed over silica gel. Elution with acetone:water (3:1) and evaporation of solvents yielded the title compound, (0.052 g).

IR (KBr), 1775 cm$^{-1}$.

NMR (DMSO-d$_6$), δ=3.34 (s, 3H); 2.52 (m, 2H); 3.70 (m, 4H); 4.95 and 5.04 (2×s, 1H); 5.05 and 5.10 (2×d, J=6 Hz, 1H); 5.43 and 5.49 (ABq, J=12 Hz, 1H); 5.63 and 5.65 (2×s, 1H); 6.36 and 6.42 (2×s, 1H); 7.33 (m, 1H); 7.73 (m, 1H); 8.12 (m, 3H); 8.40–8.85 (m, 4H); 9.31 and 9.42 (2d, J=4 Hz, 1H); 9.53 and 9.59 (2×s, 1H).

EXAMPLE 15

7β-[DL-2-(2-oxo-3-methylsulphonylimidazolidin-1-ylcarbonylamino)-2-(3-pyridyl)acetamido]-7α-hydroxyamino-3-[tetrazolo[1,5-b]pyridazin-6-yl)thiomethyl]-ceph-3-em-4-carboxylate (a)

7β-[DL-2-(2-oxo-3-methylsulphonylimidazolidin-1-ylcarbonylamino)-2-(3-pyridyl)acetamido-7α-methylthio-3-[(tetrazolo[1,5-b]pyridazin-6-yl)thiomethyl]-ceph-3-em-4-carboxylate The title compound was prepared from the 7α-methylthiocephalosporanic acid (0.35 g) of Example 13(c) by the method of Example 2(a).

IR (KBr), 1775 cm$^{-1}$.

NMR (DMSO-d$_6$), δ=1.32 and 2.20 (2×s, 3H); 3.33 (s, 3H); 3.55 (m, 2H); 3.77 (m, 4H); 4.15 and 4.60 (2×ABq, J=12 Hz, 2H); 5.04 (s, 1H); 5.63 (d, J=6 Hz, 1H); 7.38 (m, 1H); 7.75 (m, 2H); 8.56 (m, 3H); 8.80 (m, 1H); 9.78 and 9.82 (2×s, 1H).

(b)

7β-[DL-2-(2-oxo-3-methylsulphonylimidazolidin-1-ylcarbonylamino)-2-(3-pyridyl)acetamido]-7α-hydroxyamino-3-[(tetrazolo[1,5-b]pyridazin-6-yl)thiomethyl]-ceph-3-em-4-carboxylate The title compound was prepared from the the 7α-methythiocephem (0.13 g) of Example 15(a) by the method of Example 1(d).

IR (KBr), 1775 cm$^{-1}$.

NMR (DMSO-d$_6$), δ=3.33 (s, 3H); 3.52 (m, 2H); 3.72 (m, 4H); 4.15 and 4.60 (2×ABq, J=12 Hz, 2H); 5.00 and 5.01 (2×s, 1H); 5.70 (m, 1H); 7.52 (m, 1H); 7.71 and 7.74 (2×d, J=5 Hz, 1H); 8.10 (br, 1H); 7.92 (m, 1H); 8.43 and 8.46 (2×d, 1H); 8.56 (m, 2H); 8.69 (m, 1H); 8.82 and 8.87 (2×d, J=6 Hz, 1H); 9.46 and 9.65 (2×s, 1H).

EXAMPLE 16

3-[(2,5-Dihydro-6-hydroxy-2methyl-5-oxo-1,2,4-tri azin-3-yl)thiomethyl]-7α-hydroxyamino-7β-[DL-2-(3-methylsulphonyl-2-oxoimidazolidin-1-ylcarbonylamino)-2-(1,2,3-thiadiazol-4-yl)acetamido]ceph-3-em-4-carboxylic acid (a)

7β-Benzylideneamino-3-[(2,5-dihydro-6-hydroxy-2-methyl-5-oxo-1,2,4-triazin-3-yl)thiomethyl]ceph-3-em-4-carboxylic acid A suspension of 7β-amino-3-[(2,5-dihydro-6-hydroxy-2-methyl-5-oxo-1,2,4-triazin-3-yl)thiomethyl]-ceph-3-em-4-carboxylic acid (see EP 65748) (3.71 g) in dimethylformamide (50 ml) was treated with benzaldehyde (4.24 g) and the mixture was sonicated in an ultrasound bath at 25° for 0.5 hours, by which time a clear solution had resulted. After evaporation to dryness in vacuo the residue was triturated with ether to give the title compound, (4.28 g).

I.R. (KBr) 1770 cm$^{-1}$.

N.M.R. (DMSO-d$_6$), δ=3.53 and 3.73 (ABq, J=18, 2H); 3.58 (s, 3H); 4.08 and 4.35 (ABq, J=13, 2H); 5.28 (d, J=4.5, 1H); 5.62 (d, J=4.5, 1H); 7.46–7.77 (m, 5H); 8.56 (s, 1H).

(b) Benzhydryl 3-[(6-benzhydryloxy-2,5-dihydro-2-methyl-5-oxo-1,2,4-triazin-3-yl)thiomethyl]-7β-benzylideneaminoceph-3-em-4-carboxylate The product from Example 16(a) (4.02 g) in dichloromethane (50 ml) was treated dropwise over 0.5 hours with a solution of diphenyldiazomethane (3.74 g) in dichloromethane (50 ml). After stirring for a further 18 hours the solution was evaporated to dryness and the residue was triturated with ether (150 ml) to afford the title compound as a pale cream solid, (5.45 g).

I.R. (KBr), 1780 cm$^{-1}$.

N.M.R. (CDCl$_3$), δ=3.53 (s, 3H); 3.54 and 3.68 (ABq, J=19, 2H); 4.06 and 4.43 (ABq, J=13, 2H); 5.17 (d, J=5, 1H); 5.43 (d, J=5, 1H); 6.75 (s, 1H); 6.96 (s, 1H); 7.20–7.79 (m, 25H); 8.62 (s, 1H).

(c) Benzhydryl 7β-amino-3-[(6-benzhydryloxy-2,5-dihydro-2-methyl-5-oxo-1,2,4-triazin-3-yl)thiomethyl]-7α-methylthioceph-3-em-4-carboxylate The dibenzhydryl cephem (Example 16(b)) (3.02 g) in tetrahydrofuran (20 ml) was treated at −65° with a solution of potassium tert-butoxide (0.43 g) in tetrahydrofuran (10 ml), added dropwise over 1 minute. The resulting dark red solution was stirred for a further 2 minutes at −65° then methyl methanethiosulphonate (0.48 g) was added and the mixture stirred to −30° over 1 hour. The reaction mixture was added to water (50 ml) and dichloromethane (50 ml) and the dichlormethane layer separated, dried (Na$_2$SO$_4$) and evaporated in vacuo giving a foam (3.3 g).

The crude 7α-sulphenylated imine thus obtained was dissolved in methanol (10 ml) and dichloromethane (10 ml) and treated with Girard Reagent-T. After stirring for 4 hours at 25° the solution was evaporated in vacuo and the residue dissolved in dichloromethane (20 ml) and water (20 ml). The dichloromethane layer was separated, dried (Na$_2$SO$_4$) and evaporated in vacuo giving a foam. The product was purified by silica gel chromatography (dichloromethane-ethyl acetate gradient) to afford the title compound, (0.96 g).

I.R. (KBr), 1775 cm$^{-1}$.

N.M.R. (CDCl$_3$), δ=2.11 (s, 2H); 2.35 (s, 3H); 3.54 (s, 3H); 3.57 and 3.68 (ABq, J=18, 2H); 4.14 and 4.46 (ABq, J=13, 2H); 4.78 (s, 1H); 6.75 (s, 1H); 6.90 (s, 1H); 7.21–7.49 (m, 20H).

(d) Benzhydryl 3-[(6-benzhydryloxy-2,5-dihydro-2-methyl-5-oxo-1,2,4-triazin-3-yl)thiomethyl]-7β-[DL-2-(3-methylsulphonyl-2-oxoimidazolidin-1-ylcarbonylamino)-2-(1,2,3-thiadiazol-4-yl)acetamido]-7α-methylthioceph-3-em-4-carboxylate The title compound (210 mg) was prepared by the reaction of the product from Example 16(c) above (400 mg) with DL-2-(3-methylsulphonyl-2-oxoimidazolidin-1-ylcarbonylamino)-2-(1,2,3-thiadiazolyl)acetic acid [from Example 3(b)] (167 mg) by the procedure described in Example 13(b).

I.R. (KBr), 1780 cm$^{-1}$.

N.M.R. (CDCl$_3$), δ=2.18 and 2.23 (2×s, 3H); 3.21 (s, 3H); 3.33–3.56 (m, 2H); 3.51 and 3.53 (2×s, 3H); 3.75–4.08 (brm, 4H); 4.18–4.62 (m, 2H); 4.84 and 4.93 (2×s, 1H); 6.42–6.46 (m, 1H); 6.72 and 6.75 (2×s, 1H); 6.84 and 6.87 (2×s, 1H); 7.17–7.50 (m, 20H); 8.92–9.07 (br m, 2H); 9.21 and 9.23 (2×s, 1H).

(e) 3-[(2,5-Dihydro-6-hydroxy-2-methyl-5-oxo-1,2,4-triazin-3-yl)thiomethyl]-7β-[DL-2-(3-methylsulphonyl-2-oxoimidazolidin-1-ylcarbonylamino)-2-(1,2,3-thiadiazol-4-yl)acetamido]-7α-methylthioceph-3-em-4-carboxylic acid A solution of the dibenzhydryl cephem [from Example 16(d)] (210 mg) in dichloromethane (3 ml) containing anisole (260 mg) was precooled to −65° and treated with a solution of aluminium chloride (160 mg) in nitromethane (1 ml). After 0.5 hours at −65° the reaction mixture was added to saturated aqueous sodium bicarbonate (20 ml) and ethyl acetate (20 ml). The mixture was filtered to remove insoluble inorganic salts and the aqueous layer separated. Concentrated hydrochloric acid was added to pH 1.0 and the solution saturated with solid sodium chloride. Extraction with 2×20 ml portions of ethyl acetate:tetrahydrofuran (1:1), followed by drying (Na$_2$SO$_4$) and evaporation of the solvent in vacuo, afforded the title compound, (112 mg).

I.R. (KBr), 1780 cm$^{-1}$.

N.M.R. (DMSO-d$_6$), δ=2.03 and 2.23 (2×s, 3H); 3.30–3.83 (m, 12H); 4.00–4.08 and 4.30–4.37 (2×m, 2H); 5.03 and 5.04 (2×s, 1H); 6.18 (d, J=8, 1H); 8.98–9.03 (m, 1H); and 9.14 and 9.15 (2×s, 1H); 9.78 and 9.81 (2×s, 1H).

(f) 3-[(2,5-Dihydro-6-hydroxy-2-methyl-5-oxo-1,2,4-triazin-3-yl)thiomethyl]7α-hydroxyamino-7β-[DL-2-(3-methylsulphonyl-2-oxoimidazolidin-1-ylcarbonylamino)-2-(1,2,3-thiadiazol-4-yl)acetamido]ceph-3-em-4-carboxylic acid The title compound (60 mg) was prepared by reaction of the 7α-methylthiocephem [Example 16(e)] (105 mg) with mercuric acetate and hydroxylamine hydrochloride as described previously for Example 1(d).

I.R. (KBr), 1775 cm$^{-1}$.

N.M.R. (DMSO-d$_6$), δ=3.21–3.41 ((m, 2H); 3.34 (s, 3H); 3.56 and 3.57 (2×s, 3H); 3.72–3.83 (m, 4H); 3.97–4.04 and 4.28–4.35 (2×m, 2H); 4.99 and 5.02 (2×s, 1H); 6.22 (d, J=8, 1H); 6.51–6.53 (br m, 1H); 8.08 and 8.17 (2×s, 1H); 8.97 and 9.05 (2×d, J=8, 1H); 9.12 and 9.15 (2×s, 1H); 9.43 and 9.59 (2×s, 1H).

We claim:

1. A cephalosporin having the formula

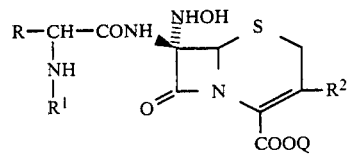

wherein

Q is hydrogen or a radical forming an in vivo hydrolyzable ester;

R is thiazolyl, thiadiazolyl, furyl or pyridyl; and the amide side chain is in the D- or DL-stereochemical form;

R$^1$ is a group of the formula

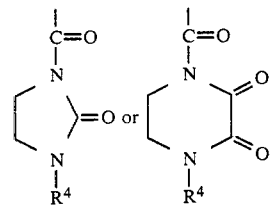

where
R$^4$ is C$_1$-C$_4$ alkyl or —SO$_2$(C$_1$-C$_4$alkyl),

R$^2$ is —CH$_2$OCOCH$_3$, —CH$_2$OCONH$_2$ or a group of the formula

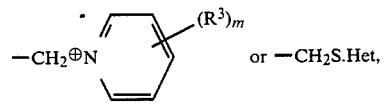

where m is 1 or 2; each R$^3$ is independently H or C$_1$-C$_4$ alkyl; and Het is a heterocyclic group which is a triazolyl, tetrazolyl, thiazolyl, isothiazolyl, oxazolyl, oxadiazolyl, triazinyl, oxodihydrotriazinyl, dioxotetrahydrotriazinyl, thiadiazolyl, benzoxazolyl, benzothiazolyl or tetrazolopyridazinyl group; one of said heterocyclic groups substituted by 1 or more groups selected from C$_1$-C$_4$ alkyl, C$_1$-C$_4$ alkoxy, halo, oxo or a group of the formula —(CH$_2$)$_p$R$^5$ where p is 0, 1, 2 or 3 and R$^5$ is —COOH, —OSO$_2$OH, —SO$_2$OH, —PO$_3$H$_2$ or —OH, with the proviso that p is not zero when Het is tetrazolyl; or a pharmaceutically-acceptable cationic salt thereof when Q is hydrogen or the group R$^2$ contains a further acidic functionality.

2. A compound of claim 1 wherein Het is attached to the adjacent sulfur atom by a carbon atom of the heterocyclic ring and is (i) thiadiazolyl, or thiadiazolyl substituted by C$_1$–C$_4$ alkyl or 2-hydroxyethyl; (ii) tetrazolyl or tetrazolyl substituted by C$_1$–C$_4$ alkyl, carboxymethyl, sulphomethyl, 2-hydroxyethyl, hydroxysulphonyloxymethyl or 2-(hydroxysulphonyloxy)ethyl; (iii) thiazolyl or thiazolyl substituted by 1 to 2 substituents each selected from C$_1$–C$_4$ alkyl and carboxymethyl; (iv) isothiazolyl or isothiazolyl substituted by 1 or 2 substituents each selected from hydroxy and carboxy; (v) benzothiazolyl or benzoxazolyl, or benzothiazolyl or benzoxazolyl substituted by hydroxy, C$_1$–C$_4$ alkoxy or halo; (vi) tetrazolopyridazinyl or tetrazolopyridazinyl substituted by carboxy; (vii) triazinyl or triazinyl substituted by C$_1$–C$_4$ alkyl and/or by 1 or 2 oxo or hydroxy groups; or (viii) triazolyl or triazolyl substituted by carboxymethyl.

3. A compound of claim 2 wherein R$^2$ is pyridiniummethyl or —CH$_2$S.Het and Het is

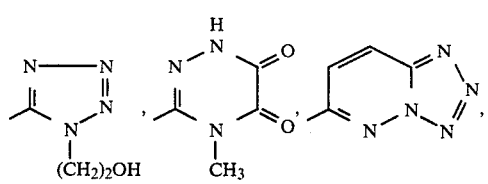

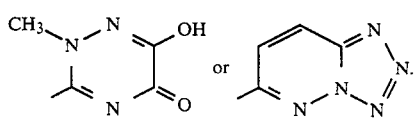

4. A compound of claim 1 wherein R is 4-thiazolyl, 1,2,3-thiadiazol-4-yl, 2-furyl or 3-pyridyl.

5. A compound of claim 3 wherein R is 4-thiazolyl, 1,2,3-thiadiazol-4-yl, 2-furyl or 3-pyridyl.

6. A compound of claim 1 where R$^4$ is CH$_3$, C$_2$H$_5$ or —SO$_2$CH$_3$.

7. A compound of claim 3 wherein R$^4$ is CH$_3$, C$_2$H$_5$ or —SO$_2$CH$_3$.

8. A compound of claim 4 wherein R$^4$ is CH$_3$, C$_2$H$_5$ or —SO$_2$CH$_3$.

9. A compound of claim 5 wherein R$^4$ is CH$_3$, C$_2$H$_5$ or —SO$_2$CH$_3$.

10. A compound of claim 9 wherein R$^1$ is

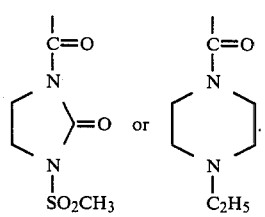

11. A compound of claim 1 wherein Q is hydrogen.
12. A compound of claim 3 wherein Q is hydrogen.
13. A compound of claim 8 wherein Q is hydrogen.
14. A compound of claim 10 wherein Q is hydrogen.

15. The compound of claim 14 wherein R is 4-thiazolyl, R$^2$ is

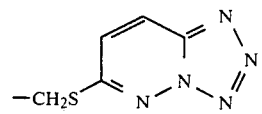

and R$^3$ is

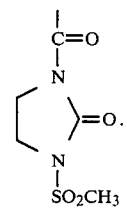

16. The compound of claim 14 wherein R is 1,2,3-thiadiazol-4-yl, R$^2$ is

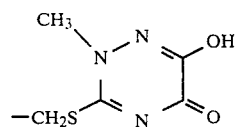

and R$^3$ is

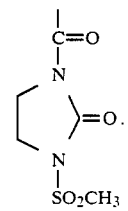

17. The compound of claim 14 wherein R is 1,2,3-thiadiazol-4-yl, R$^2$ is pyridininummethyl and R$^3$ is

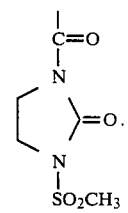

18. The compound of claim 14 wherein R is 1,2,3-thiadiazol-4-yl, R$^2$ is

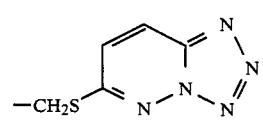

and R$^3$ is

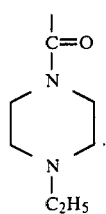

19. The compound of claim 14 wherein R is 3-pyridyl, $R^2$ is

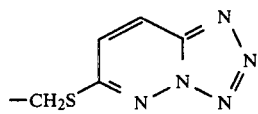

and $R^3$ is

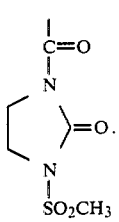

20. A compound of claim 1 wherein Q is a radical forming an in vivo hydrolyzable ester.

21. A compound of claim 3 wherein Q is a radical forming an in vivo hydrolyzable ester.

22. A compound of claim 8 wherein Q is a radical forming an in vivo hydrolyzable ester.

23. A compound of claim 10 wherein Q is a radical forming an in vivo hydrolyzable ester.

24. A compound of claim 20 wherein the radical is —$CH_2OCOC(CH_3)_3$, —$CH_2OCOCH_3$, —$CH(CH_3)OCOCH_3$, —$CH(CH_3)OCOOC_2H_5$,

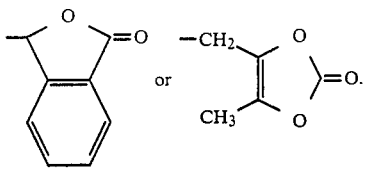

25. A compound of claim 23 wherein the radical is —$CH_2OCOC(CH_3)_3$, —$CH_2OCOCH_3$, —$CH(CH_3)OCOCH_3$, —$CH(CH_3)OCOOC_2H_5$,

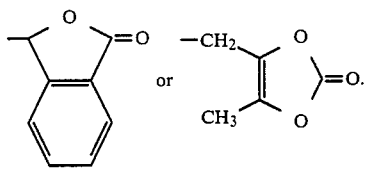

26. A pharmaceutical composition comprising an antibacterially effective amount of a compound of claim 1 and a pharmaceutically-acceptable diluent or carrier suitable for parenteral administration in the treatment of bacterial infection in man.

27. A method of treating a bacterial infection in man which comprises parenteral administration of an antibacterially effective amount of a compound of claim 1.

28. A cephalosporin ester having the formula

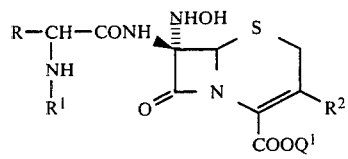

wherein $Q^1$ is a conventional carboxy protecting group;

R is thiazolyl, thiadiazolyl, furyl or pyridyl; and the amide side chain is in the D- or DL-stereochemical form;

$R^1$ is a group of the formula

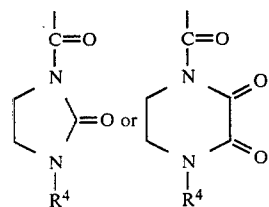

where $R^4$ is $C_1$-$C_4$ alkyl or —$SO_2(C_1$-$C_4$alkyl), $R^2$ is —$CH_2OCOCH_3$, —$CH_2OCONH_2$ or a group of the formula

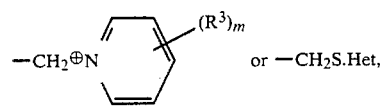

where m is 1 or 2; each $R^3$ is independently H or $C_1$-$C_4$ alkyl; and Het is a heterocyclic group which is a triazolyl, tetrazolyl, thiazolyl, isothiazolyl, oxazolyl, oxadiazolyl, triazinyl, oxodihydrotriazinyl, dioxotetrahydrotriazinyl, thiadiazolyl, benzoxazolyl, benzothiazolyl, or tetrazolopyridazinyl group; one of said heterocyclic groups substituted by 1 or more groups selected from $C_1$-$C_4$ alkyl, $C_1$-$C_4$ alkoxy, halo, oxo or a group of the formula —$(CH_2)_pR^5$ where p is 0, 1, 2 or 3 and $R^5$ is —COOH, —$OSO_2OH$, —$SO_2OH$, —$PO_3H_2$ or —OH, with the proviso that p is not zero when Het is tetrazolyl.

29. A compound of claim 28 wherein $Q^1$ is t-butyl or benzhydryl; R is 4-thiazolyl, 1,2,3-thiadiazol-4-yl, 2-furyl or 3-pyridyl; $R^2$ is pyridiniummethyl or —$CH_2S$.-Het and Het is

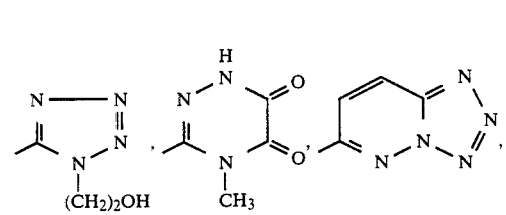

-continued
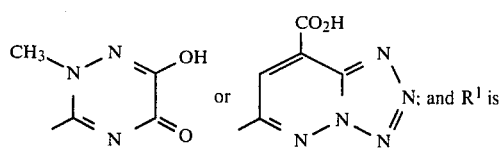 or 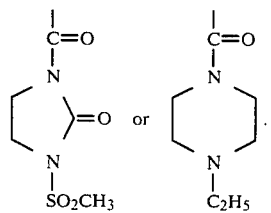
; and $R^1$ is
* * * * *